US011291735B2

(12) United States Patent
Demina et al.

(10) Patent No.: US 11,291,735 B2
(45) Date of Patent: Apr. 5, 2022

(54) DRUG DELIVERY SYSTEM BASED ON JCV-VLP

(71) Applicant: LIFE SCIENCE INKUBATOR BETRIEBS GMBH & CO. KG, Bonn (DE)

(72) Inventors: Victoria Demina, Bonn (DE); Heiko Manninga, Goettingen (DE); Armin Götzke, Wuerzburg (DE); Alexander Glassmann, Cologne (DE)

(73) Assignee: LIFE SCIENCE INKUBATOR BETRIEBS GMBH & CO. KG, Bonn (DE)

( * ) Notice: Subject to any disclaimer, the term of this patent is extended or adjusted under 35 U.S.C. 154(b) by 299 days.

(21) Appl. No.: 16/354,739

(22) Filed: Mar. 15, 2019

(65) Prior Publication Data
US 2019/0201549 A1 Jul. 4, 2019

Related U.S. Application Data

(63) Continuation of application No. 16/018,110, filed on Jun. 26, 2018, now abandoned, which is a continuation of application No. 14/383,267, filed as application No. PCT/EP2013/000656 on Mar. 6, 2013, now abandoned.

(30) Foreign Application Priority Data

Mar. 6, 2012 (EP) .................................... 12001507

(51) Int. Cl.
*A61K 48/00* (2006.01)
*C12N 15/86* (2006.01)
*C12N 7/00* (2006.01)

(52) U.S. Cl.
CPC ............ *A61K 48/0025* (2013.01); *C12N 7/00* (2013.01); *C12N 15/86* (2013.01); A61K 48/00 (2013.01); *C12N 2710/22022* (2013.01); *C12N 2710/22023* (2013.01); *C12N 2710/22041* (2013.01); *C12N 2710/22042* (2013.01); *C12N 2710/22043* (2013.01); *C12N 2710/22071* (2013.01); *C12N 2710/24023* (2013.01); *C12N 2710/24042* (2013.01); *C12N 2710/24043* (2013.01); *C12N 2710/24071* (2013.01)

(58) Field of Classification Search
None
See application file for complete search history.

(56) References Cited

U.S. PATENT DOCUMENTS

| | | | |
|---|---|---|---|
| 6,238,859 | B1 | 5/2001 | Luke et al. |
| 2003/0044961 | A1 | 3/2003 | Luke et al. |
| 2006/0052296 | A1 | 3/2006 | Khalili |
| 2007/0009921 | A1 | 1/2007 | Walter et al. |
| 2012/0258443 | A1 | 10/2012 | Gorelik et al. |

FOREIGN PATENT DOCUMENTS

| | | |
|---|---|---|
| CN | 1346366 A | 4/2002 |
| JP | 2003/61693 A | 3/2003 |
| JP | 2007-197441 A | 8/2007 |
| WO | 98/48841 A1 | 11/1998 |
| WO | 2010/090757 A1 | 8/2010 |

OTHER PUBLICATIONS

Goldmann et al. J Virol. May 1999;73(5):4465-9.*
Louboutin et al. Nature Methods. 2010. 7(11): 905-907.*
Schulz JB. J Neural Transm Suppl. 2006;(70):467-76.*
GenBank: AAC59325.1 VP1 [JC polyomavirus], dated Apr. 13, 1998.*
Chang et al. Human JC virus-like particles as a gene delivery vector. Expert Opin. Biol. Ther. (2011) 11(9):1169-1175.*
Chapagain, Moti L. et al., "Human Polyomavirus JC (JCV) Infection of Human B Lymphocytes: A Possible Mechanism for JCV Transmigration across the Blood-Brain Barrier," The Journal of Infectious Diseases, vol. 202 (2): 184-191 (2010).
Chou, Meng-Ing et al., "In vitro and in vivo targeted delivery of IL-10 interfering RNA by JC virus-like particles," Journal of Biomedical Science, vol. 17:51, 9 pages (2010).
Jaeger, Laura B et al., "Migration of JC virus across the human blood-brain barrier occurs via clathrin-mediated endocytosis," Journal of Neurovirology, vol. 15(Suppl. 1):37, Poster No. P80, 9th International Symposium on Neurovirology, 1 page (2009).
Krauzewicz, N. et al., "Sustained ex vivo and in vivo transfer of a reporter gene using polyoma virus pseudocapsids," Gene Therapy, vol. 7:1094-1102 (2000).
Rempe, Ralf et al., "Transport of Poly(n-butylcyano-acrylate) nanoparticles across the blood-brain barrier in vitro and their influence on barrier integrity," Biochemical and Biophysical Research Communications, 6 pages, (2011).
International Search Report and Written Opinion for Application No. PCT/EP2013/000656, 9 pages, dated May 7, 2013.
B. F. Sabath et al.: "Traffic of JC Virus from Sites of Initial Infection to the Brain: The Path to Progressive Multifocal Leukoencephalopathy", The Journal of Infectious Diseases, vol. 186, Suppl 2, p. S180-S186 (2002).
J. R. Kanwar et al.: "Nanoparticles in the treatment and diagnosis of neurological disorders: untamed dragon with fire power to heal", Nanomedicine: Nanotechnology, Biology, and Medicine, vol. 8, p. 399-414 (2012).
M. L. Chapagain et al.: "Polyomavirus JC infects human brain microvascular endothelial cells independent of serotonin receptor 2A", Virology, vol. 364, No. 1, English Abstract, pp. 55-63 (2007).
C. Chang et al.: "Human JC virus-like particles as a gene delivery vector", Expert Opin. Biol. Ther., vol. 11, No. 9 pp. 1169-1175 (2011).

(Continued)

*Primary Examiner* — Nianxiang Zou
(74) *Attorney, Agent, or Firm* — Sughrue Mion, PLLC

(57) ABSTRACT

The invention relates to VLP derived from human polyoma virus loaded with a drug (cargo) as a drug delivery system for transporting said drug into the CNS, in particular of living humans.

12 Claims, 10 Drawing Sheets

Figure 1A:
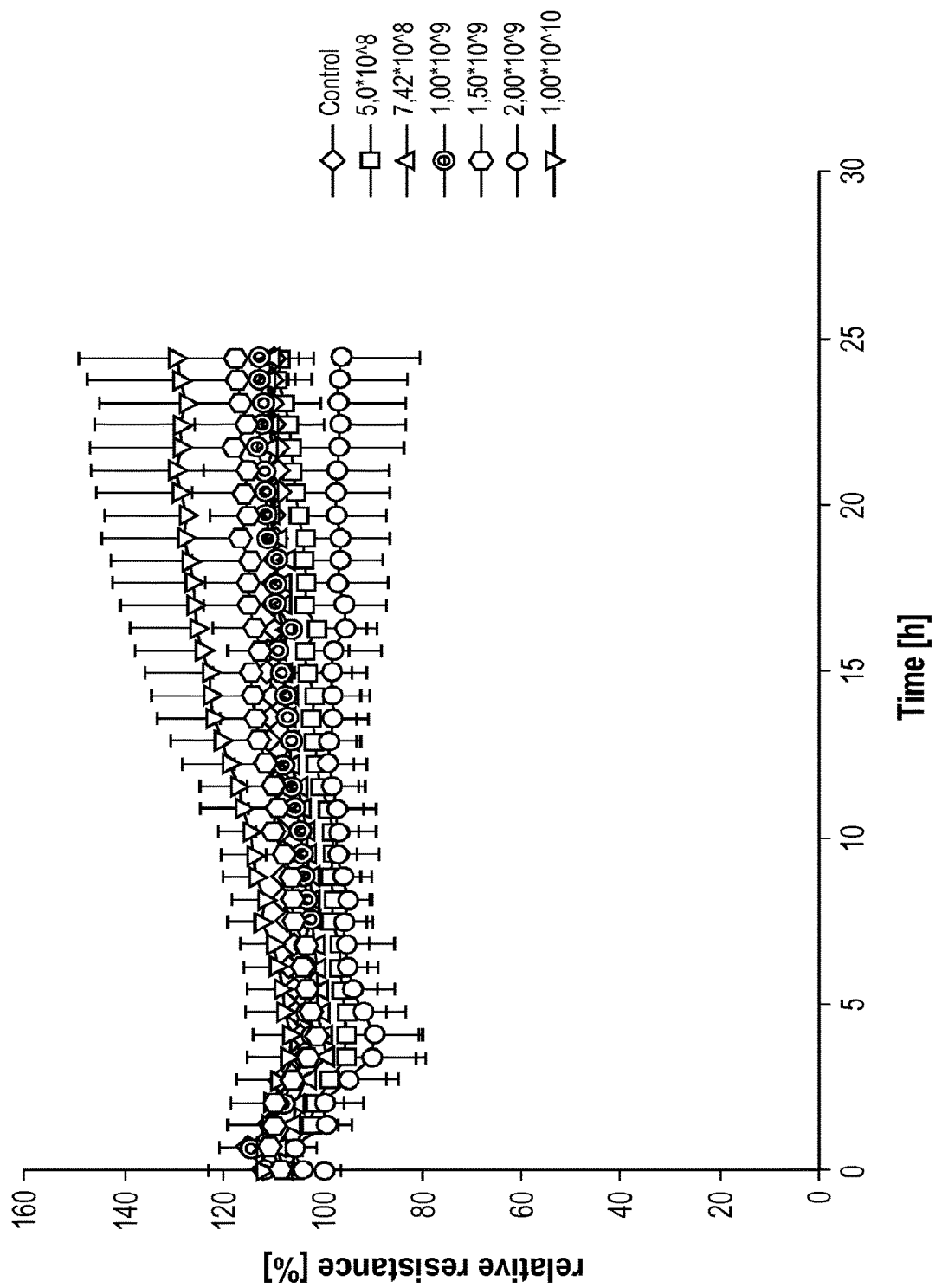
Figure 1B:
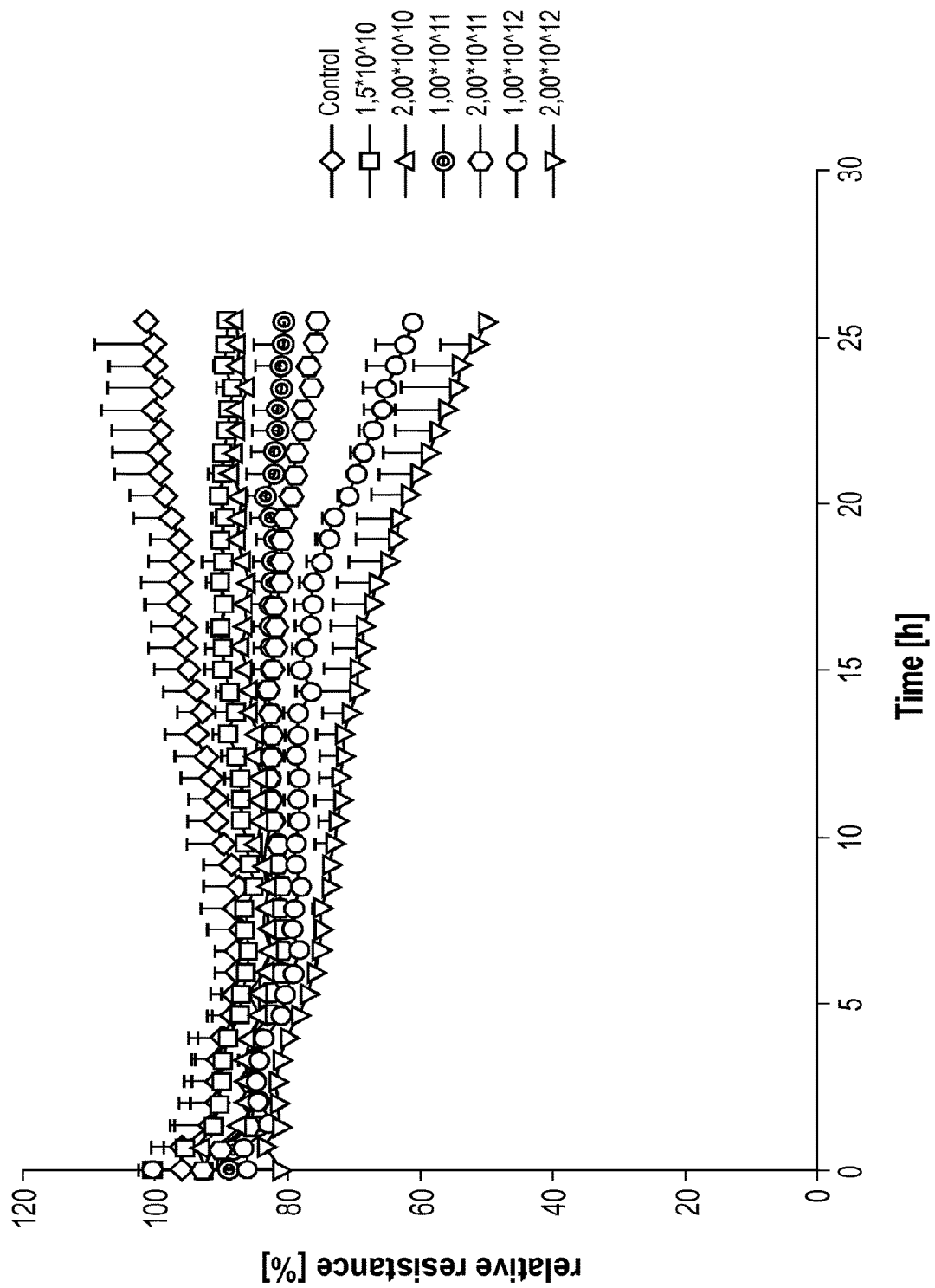
Figure 2:
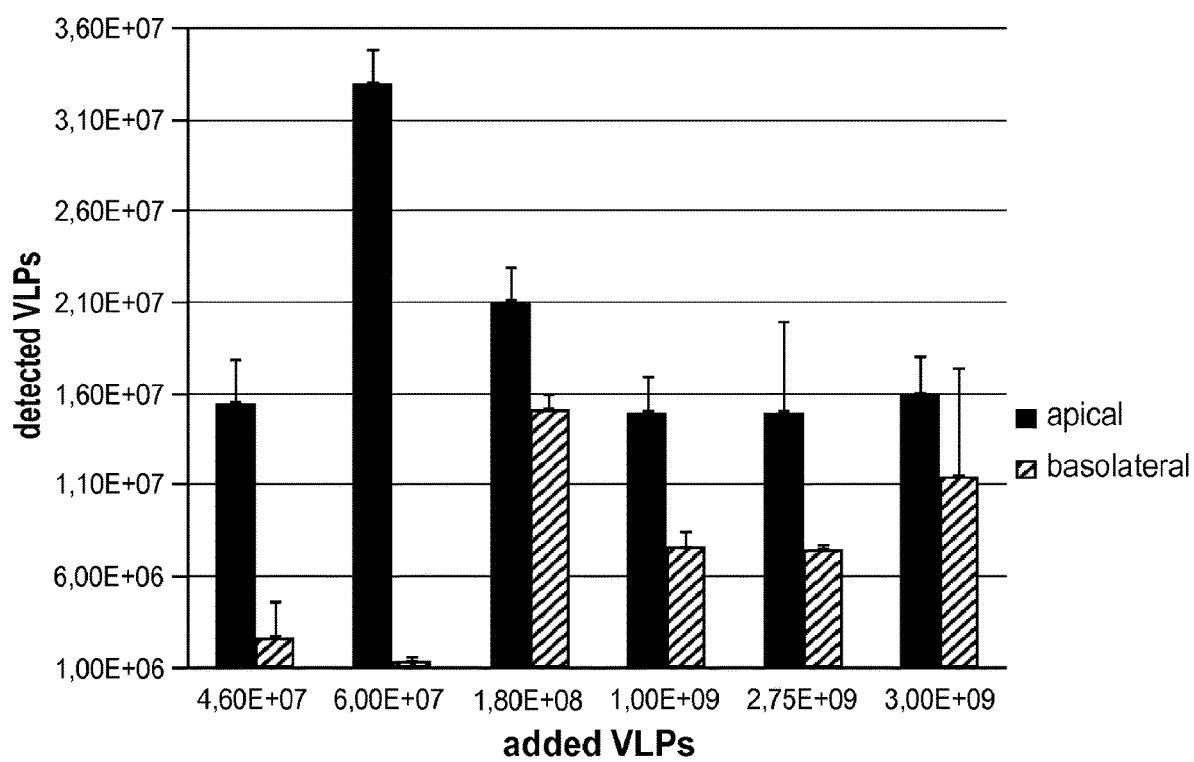

Specification includes a Sequence Listing.

(56) References Cited

OTHER PUBLICATIONS

W. Ou et al.: "The major capsid protein, VP1, of human JC virus expressed in *Escherichia coli* is able to self-assemble into a capsid-like particle and deliver exogenous DNA into human kidney cells" Journal of General Virology, vol. 80, p. 39-46 (1999).
M. Wang et al.: "Inhibition of Simian Virus 40 Large Tumor Antigen Expression in Human Fetal Glial Cells by an Antisense Oligodeoxynucleotide Delivered by the JC Virus-Like Particle" Human Gene Therapy, vol. 15, pp. 1077-1090 (2004).
M.-I. Chou et al.: "In vitro and in vivo targeted delivery of IL-10 interfering RNA by JC virus-like particles" Journal of Biomedical Science, vol. 17, pp. 1-9 (2010).
Louboutin et al. Efficient CNSgene delivery by intravenous injection (Nature Methods, 2010, 7(11):905-909).
Goldmann et al. Molecular cloning and expression of major structural protein VP1 of the human polyomavirus JC virus: formation of virus-like particles useful for immunological and therapeutic studies. J Virol. May 1999; 73(5):4465-9.
GenBank: AAC59325.1, VP1 [JC polyomavirus], dated VRL Apr. 13, 1998.
Schulz JB. Anti-apoptotic gene therapy in Parkinson's disease. J Neural Transm Suppl. 2006;(70):467-76.
Qu et al. Nuclear Entry Mechanism of the Human Polyomavirus JC Virus-like Particle. J. Biol. Chem., 279: 27735-27742, 2004.

\* cited by examiner

DRUG DELIVERY SYSTEM BASED ON JCV-VLP

CROSS REFERENCE TO RELATED APPLICATIONS

This application is a continuation of U.S. application Ser. No. 16/018,110, filed Jun. 26, 2018, which is a continuation of U.S. application Ser. No. 14/383,267, filed Sep. 5, 2014 (abandoned), which is a National Stage Entry of PCT/EP2013/000656, filed Mar. 6, 2013, which claims priority from European Application No. 12001507.8, filed Mar. 6, 2012, the contents of all of which are incorporated herein by reference.

FIELD OF THE INVENTION

The invention relates to the use of virus like particles (VLP) of the type of human polyoma virus for the use as drug delivery system.

BACKGROUND OF THE INVENTION

One of the major challenges in modern medicine is the drug delivery. Drug delivery to a selected site of action (e.g. a selected organ, tissue, cell type, or microcompartment of a cell, etc.) is called drug targeting. By drug targeting an increase of drug concentration at this specific site becomes possible even with a systemic application of the drug. Additionally, contrary to the ordinary systemic application, the rest of the body is not or only to a lower extend exposed to the drug. This leads to a reduced risk of adverse side effects and can allow a higher dosing of the drug. Furthermore, very toxic drugs (e.g. cytotoxic agents used in cancer therapeutics) may be applicable to humans for the first time, since their toxic side effects are minimized by the drug delivery system. In some cases, another advantage of drug targeting is the prevention of early inactivation (metabolism), unwanted adsorption, excretion or unwanted modification of the drug, since the drug is protected by the mode of delivery.

Drug delivery into the central nervous system (CNS), in particular into the brain, is a great challenge, since the active ingredients at first have to cross the blood-brain barrier and then have to reach the target cells.

The blood-brain barrier is formed by the endothelium of the capillaries. These endothelial cells are tightly connected by so-called "tight junctions" to each other and therewith prevent the entry of substances above a certain molecular weight size into the CNS. The blood-brain barrier thus serves as an effective protective barrier. It guarantees on the one hand the supply of nutrients to the CNS and, on the other hand, enables the removal of metabolic products out of the CNS.

The main concern is the transport of hydrophilic substances across the blood-brain barrier. Nearly 95% of all effective in vitro drug candidates are not able to pass the BBB in pharmacologically active concentrations. Therefore, to reach adequate pharmacologically concentrations of the drug within the CNS, the treatment of many CNS diseases such as brain tumors or CNS infections require high plasma concentrations of the drug. This includes the risk of adverse side effects. In pharmaceutical research therefore ways are sought to improve the transport of drugs, in particular hydrophilic agents, over the BBB into the CNS.

Some approaches use lipophilic particles, which allow a receptor-mediated transport across the blood-brain barrier. For this purpose, for example, in particular transport systems of nanoparticles have been developed. Nanoparticles are usually composed of polymers and have a size of 10-1000 nm. Mostly they are surface modified.

These nanoparticles often face the problem that they are exported from the CNS by efflux pumps which are expressed in the BBB. Furthermore, it has been shown that they affect the integrity of the BBB (Rempe et al., Biochem Bioph Res Comm 2011, 406 (1): 64-69). Thus, the protective function of the BBB is put under risk, including the risk of side effects by the entry of unwanted substances or infective entities into the CNS. This substantial disadvantage is critical for the clinical application of nanoparticles as drug delivery systems.

Other possible drug delivery systems are under discussion. For example, it is known that pseudocapsids from VP1 protein of murine polyomavirus associated with β-galactosidase-coding DNA can be used to deliver that DNA into the brain after intravenous administration, leading to the expression of β-galactosidase in the brain (Krauzewicz et al. Gene Therapy 2000, 7, 1094-1102; see also WO 98/48841 A1). However, these observations do not provide sound insights into the suitability of VLP, in particular VLP derived from human Polyoma virus and loaded with a cargo, as a drug delivery system for the CNS.

It is therefore an objective of the present invention to provide a drug delivery system that allows drug transport into CNS cells, i.e. a drug delivery over the BBB.

SUMMARY OF THE INVENTION

The inventors have found in a BBB model based on primary porcine endothelial cells that VLP of human JCV origin loaded with a nucleic acid coding for a reporter protein can cross the BBB and deliver the nucleic acid to CNS cells, where the nucleic acid is expressed. This model is considered representative of the physiologically intact BBB in vivo. Therefore it shows that the VLP, and not just the active substance alone, cross the BBB and enter into the CNS. Accordingly, VLP derived from human Polyoma virus and loaded with a cargo substance is suitable as a drug delivery system into the CNS, in particular into the brain.

The inventors furthermore have found that the crossing of the loaded VLP does neither require nor lead to a loss of integrity or increased permeability of the BBB. Hence, the integrity of the BBB is not substantially affected by the VLP. Thus VLP can be used as drug delivery system into the CNS without the substantial risk of adverse side effects due to the entry of unwanted substances or infectious entities into the CNS.

According to the invention, VLP derived from human polyoma virus and loaded with a cargo are used to cross the BBB together with the cargo. Importantly, the crossing of the BBB by the VLP enables the VLP to exhibit its function of targeting specific cell populations within the brain, i.e. deliver the cargo to targeted cells. In the context of the invention said delivery comprises a delivery to, in or into the targeted cells. Hence according to the invention a functional VLP crosses the BBB together with the cargo.

The cargo, preferably an active substance, is preferably fully encapsulated in the hull of the VLP. This however does not exclude that the VLP additionally can be associated with the active substance, e.g. by way of binding of the active substance to outside structures of the hull. Some molecules of the active substance might even be incompletely encapsulated within the hull. However, at least a part of the molecules of the active substance is fully encapsulated in the hull.

Hence according to the invention a composition of VLP derived from human polyoma virus and an active substance is provided as a drug delivery system, wherein at least 1%, at least 2%, at least 3%, at least 5%, at least 7%, at least 10%, at least 15%, at least 20%, at least 25%, at least 30%, at least 40%, at least 50%, at least 60%, more preferably at least 70%, at least 75%, at least 80%, at least 85%, at least 90%, at least 95%, at least 97%, at least 98%, at least 99% or 100% of the total amount of the active substance (cargo) is encapsulated in the hull of the VLP.

In a most preferred embodiment of the invention the VLP of the composition are non-aggregated. Non-aggregated means that the VLP are able to form separated particles, when being suspended in water.

In one aspect of the invention thus a drug delivery system for the CNS is provided which allows a co-transport of the VLP and the active substance. The transport can be either active or passive. Interestingly the inventors furthermore found that the VLP are not or not substantially removed from the CNS by efflux transporters of the BBB.

The VLP as of the invention do not require a surface treatment or the use of additives in order to efficiently cross the BBB and enter into the CNS. Hence in one aspect of the invention a drug delivery system is provided with particulate structures without any further surface treatment or modification and without the use of additives. The drug delivery system preferably is cell-free.

As outlined above, according to the invention, the VLP are used for drug delivery into the CNS, in particular into the brain. The delivery into the brain can enable a drug targeting into specific cells, e.g. by taking advantage of the natural tropism of the human Polyoma virus (specifically of JCV).

DETAILED DESCRIPTION OF THE INVENTION

A virus-like particle (VLP) derived from human polyoma virus, in particular from JCV, is used for drug delivery according to the present invention preferably comprising at least one VP1. The VLP is preferably composed of a hull build up of VP1 assembled into pentameric structures. Preferably, the VLP is composed of several VP1, in particular several VP1 pentamers, especially 72 VP1 pentamers. However, the VLP may optionally comprise further molecules incorporated into the hull. The structure molecules assembling the VLP can either be identical to the native Polyoma virus proteins or can be modified in order to optimize the VLP characteristics.

Furthermore, the VLP according to the present invention further comprises a cargo load. In a particular preferred embodiment of the invention the major part of the total amount of the cargo is fully incorporated into the hull. To describe the full encapsulation of the cargo molecule by the VLP the term "loaded" is used. Hence a "loaded VLP" is a VLP with a fully encapsulated cargo.

Said cargo load may be any molecule or composition fitting inside the space surrounded by the hull. Preferably, the cargo load is a cytotoxic agent, a detectable agent such as a radionuclide, a protein, a peptide or a nucleic acid, in particular selected from the group consisting of nucleic acids encoding a desired protein such as mRNA, cDNA, a plasmid or vector, inhibitory nucleic acids such as siRNA or miRNA and nucleic acids having catalytic activity such as a ribozyme. The cargo load is sometimes referred hereinafter as the "active substance", "drug substance" or "active ingredient". As long as not otherwise explicitly mentioned these terms are used as synonyms.

VLP may be produced by providing the desired components, in particular VP1, optionally VP2, optionally VP3 or a mixture thereof and optionally the cargo load, in solution and allowing the components to assembly into the VLP. For example, mixing of the components may be performed under conditions where no or only limited VLP assembly occurs, such as at low $Ca^{2+}$ concentrations and/or reducing conditions, and after addition of all desired components the conditions are changed into those favorable for VLP assembly, such as higher $Ca^{2+}$ concentrations and/or oxidizing conditions. However, VLP production may also occur in vivo. In particular, the components of the VLP may be coexpressed in a host cell and the VLP assemble inside the host cell or upon lysis or disruption of the host cell.

The term "human polyoma virus" refers to the family of human polyoma virus, comprising JCV, BK and SV40. In a particularly preferred embodiment the human polyoma virus is JCV.

"VP1" or "virus protein 1" according to the present invention refers to a protein which is identical to or is derived from the natural VP1 of the JC virus having the amino acid sequence according to SEQ ID NO: 1. A protein derived from the natural VP1 of the JC virus preferably has an amino acid sequence homology or identity with the amino acid sequence according to SEQ ID NO: 1 of at least 60%, more preferably at least 70%, at least 75%, at least 80%, at least 85%, at least 90%, at least 95%, at least 97%, at least 98% or at least 99% over a sequence of at least 100 contiguous amino acids, preferably at least 150, at least 200, at least 250 or at least 300 contiguous amino acids. Most preferably, the amino acid homology or identity is calculated over the entire length of the natural JCV-VP1. The terms "VP1 derived from the natural VP1 of the JC virus" and "VP1 derived from JC virus" in particular also include VP1 which is identical to the natural VP1 of the JC virus.

The term "VP1" according to the invention also encompasses fractions and derivatives of the natural VP1 which are capable of assembling into VLP. Preferably, said fractions and derivatives of VP1 at least comprise amino acids 32 to 316 of the amino acid sequence according to SEQ ID NO: 1 or a derivative thereof having a homology or identity with the amino acid sequence from amino acid position 32 to 316 of SEQ ID NO: 1 of at least 60%, more preferably at least 70%, at least 75%, at least 80%, at least 85%, at least 90%, at least 95%, at least 97%, at least 98% or at least 99% over a sequence of at least 100 contiguous amino acids, preferably at least 150, at least 200, at least 250 or at least 300 contiguous amino acids, preferably over the entire sequence.

A VP1 according to the present invention may also include a heterologous nuclear localization signal (NLS). Preferably, this NLS is introduced in front of or into the N-terminus of NP1, in particular into the first 30, the first 25, the first 20, the first 15 or the first 10 amino acids of VP1. For example, an NLS as described in WO 2009/036933 (for example page 10, lines 4 to 13 and FIG. 4A) or in Shishido-Hara et al. (Shishido-Hara, Y., Hara, Y., Larson, T., Yasui, K., Nagashima, K. & Stoner, G. L. Analysis of Capsid Formation of Human Polyomavirus JC (Tokyo-1 Strain) by a Eukaryotic Expression System: Splicing of Late RNAs, Translation and Nuclear Transport of Major Capsid Protein VP1, and Capsid Assembly. Journal of Virology 74, 1840-1853 (2000).

According to one embodiment, the amino acid sequence according to SEQ ID NO: 5 is introduced into the N-terminal part of VP1, in particular between the amino acids corresponding to amino acids 9 and 10 of SEQ ID NO: 1.

"VP2" or "virus protein 2" according to the present invention refers to a protein which is identical to or is derived from the natural VP2 of the JC virus having the amino acid sequence according to SEQ ID NO: 3. A protein derived from the natural VP2 of the JC virus preferably has an amino acid sequence homology or identity with the amino acid sequence according to SEQ ID NO: 3 of at least 60%, more preferably at least 70%, at least 75%, at least 80%, at least 85%, at least 90%, at least 95%, at least 97%, at least 98% or at least 99% over a sequence of at least 100 contiguous amino acids, preferably at least 150, at least 200, at least 250 or at least 300 contiguous amino acids. Most preferably, the amino acid homology or identity is calculated over the entire length of the natural JCV-VP2. The terms "VP2 derived from the natural VP2 of the JC virus" and "VP2 derived from JC virus" in particular also include VP2 which is identical to the natural VP2 of the JC virus.

The term "VP2" according to the invention also encompasses fractions and derivatives of the natural VP2 which are capable of assembling into VLP together with VP1. Preferably, said fragments of VP2 at least comprise amino acids 214 to 318 of the amino acid sequence according to SEQ ID NO: 3 or a derivative thereof having a homology or identity with the amino acid sequence from amino acid position 214 to 318 of SEQ ID NO: 3 of at least 60%, more preferably at least 70%, at least 75%, at least 80%, at least 85%, at least 90%, at least 95%, at least 97%, at least 98% or at least 99% over a sequence of at least 100 contiguous amino acids, preferably at least 150, at least 200, at least 250 or at least 300 contiguous amino acids, preferably over the entire sequence.

A "peptide" according to the present invention may be composed of any number of amino acids of any type, preferably naturally occurring amino acids, which preferably are linked by peptide bonds. In particular, a peptide comprises at least 3 amino acids, preferably at least 5, at least 7, at least 9, at least 12 or at least 15 amino acids. Furthermore, there is no upper limit for the length of a peptide. However, preferably a peptide according to the invention does not exceed a length of 500 amino acids, preferably 300, 250, 200, 150 or 120 amino acids.

The expression "comprise", as used herein, besides its literal meaning also includes and specifically refers to the expressions "consist essentially of" and "consist of". Thus, the expression "comprise" refers to embodiments wherein the subject-matter which "comprises" specifically listed elements does not comprise further elements as well as embodiments wherein the subject-matter which "comprises" specifically listed elements may and/or indeed does encompass further elements. Likewise, the expression "have" is to be understood as the expression "comprise", also including and specifically referring to the expressions "consist essentially of" and "consist of".

Administration Methods

The VLP of the invention can be administered via various routes. Particularly preferred are dosage forms which allow a systemic effect the active substance. Most preferred are dosage forms which are administered orally or parenterally, in particular intravenously.

Manufacturing Methods

Manufacturing of Virus-Like Particles

In a further aspect, the present invention provides a method for producing the virus-like particles according to the present invention. This method in particular comprises the steps of (a) providing a viral protein VP1 which is derived from JC virus;

(b) optionally providing a viral protein VP2 and or VP3, preferably VP2, which is derived from JC virus and mixing the VP1 with the VP2 (and/or VP3);

(c) allowing the VP1 and optionally the VP2 (and/or VP3) to assembly into virus-like particles.

The method preferably further comprises the step of providing a cargo load and mixing the VP1 and optionally the VP2 and/or VP3 with the cargo load. Preferred is a mixture between VP1 and VP2.

Upon assembly of the VLP, the cargo load preferably is encapsulated inside the VLP. Preferably, at least one VLP carries a cargo load, more preferably at least 1%, at least 2%, at least 3%, at least 5%, at least 7%, at least 10%, at least 15%, at least 20%, at least 25%, at least 30%, at least 40%, at least 50%, at least 60%, at least 70%, at least 80%, at least 90%, at least 95%, at least 97%, at least 98% or at least 99% or 100% of the assembled VLP carry a cargo load.

The assembly of the virus-like particles preferably occurs in solution, more preferably in an aqueous solution. Allowing the assembly of the VLP preferably includes adjusting the $Ca^{2+}$ ion concentration in the solution to a level where assembly of VLP can occur. Said $Ca^{2+}$ ion concentration in particular is in the rage of from 0.1 mM to 5 mM, preferably from 0.2 mM to 3 mM, more preferably from 0.5 mM to 2 mM or from 0.8 mM to 1.2 mM, most preferably about 1 mM. Furthermore, allowing the assembly of the VLP preferably occurs under oxidizing conditions, in particular in the absence of significant concentrations of reducing agents such as DTT, DTE or mercaptoethanol.

Provision of the viral proteins and allowing the VLP assembly may be performed simultaneously. In particular, the viral proteins are provided under conditions where VLP assembly may occur. In preferred embodiments, provision of the viral proteins and VLP assembly is performed in vivo. In particular, the VLP are assembled inside the host cells expressing the viral proteins or upon lysis or disruption of the host cells.

Assembly of the VLP may for example be performed as described in EP 0 862 633, the disclosure of which is herein incorporated by reference.

Delivery Methods

The present invention further provides a method of delivering a substance or composition into a target cell in the central nervous system using the virus-like particles according to the present invention. The method preferably comprises the steps of (a) providing a virus-like particle according to the present invention which comprises the substance or composition as cargo load; and (b) administering the virus-like particle into the living body, preferably into a human.

The target cell may be a natural target cell of the JC virus.

The active substance or composition can be of any kind or nature. In a preferred embodiment the active substance is a nucleic acid, in particular a nucleic acid encoding a protein or peptide or an inhibitory nucleic acid such as siRNA or miRNA. In another preferred embodiment the active substance is a protein or peptide. In yet another embodiment of the invention the active substance is a small molecule, in particular a negatively charged small molecule. The active substance can also be a mixture of various active substances.

The active substance preferably is a cytotoxic agent.

Furthermore, the invention pertains to VLPs in general, which can be used as a drug delivery system for the treatment or diagnosis of neurological, neuronal or neurodegenerative disorders such as in particular multiple sclerosis, Parkinson's disease or Alzheimer's disease.

In a preferred embodiment the VLP is transported in, to or into oligodendrocytes.

EXAMPLES

VP1-VLPs in Blood-Brain-Barrier (BBB) Model In Vitro

This in vitro experiment shows the ability of the VLPs to cross the BBB in a model system that matches the organisation and properties of the human BBB. In the model system, porcine primary brain endothelial cells (PBCEC) were used which are capable to form the blood-brain-barrier in vitro (Angelow S, Zeni P and Galla H J "Usefulness and limitation of primary cultured porine horoid plexus epithel cells as an in vitro model to study drug transport at the blood-CSF barrier", Adv Drug Delivery 2004; 56(12): 1859-73).

PBCEC preparation and cultivation was conducted as described by Rempe et al., BBRC, 2011: Transport of Poly-(n-butylcyano-acrylate) nanoparticles across the blood-brain-barrier in vitro and their influence on barrier integrity.

The effect of cargo-containing VLPs on the PBCEC in Transwell filter system was explored with the help of relative transendothelial electrical resistance measurement (TEER) (Rempe et al., 2011). To establish a quantitative proof of the delivery, we used Plasmid DNA as cargo. The integrity of the blood-brain-barrier was not affected by VP1-VLPs under any circumstances and concentrations.

To verify the cargo transport through the blood-brain-barrier in vitro, the plasmid DNA was packed into the VLPs as described in Goldmann et al. 1999 (Journal of Virology: Molecular cloning and expression of major structural protein VP1 of the human polyoma virus: formation of virus like particles useful for immunological and therapeutic studies and measured quantitatively by specific qPCR). The copies of plasmid DNA were quantified on the apical and basolateral sides in the BBB in vitro model. The apical side is where the VLPs were added (the blood vessel lumen in vivo), the basolateral side refers to the brain. The quantitative proof of plasmid DNA on the basolateral side represents the VLP-mediated passage of the molecules through the brain endothelial cells, respectively the cargo delivery through the blood-brain-barrier.

1. Reporter Gene Delivery and Expression In Vivo

Reporter gene delivery experiment were planned to show the capabilities of JC VP1-VLPs to deliver the substances into the cells and organs in the living organism. In this case the reporter gene expression is one of the best methods to demonstrate not only the delivery, but the functionality of the delivered substance too (Hoffman, R. M., 2005: THE MULTIPLE USES OF FLUORESCENT PROTEINS TO VISUALIZE CANCER IN VIVO. Nat. Rev. Cancer; 5(10): 796-806).

Materials

The deferent VP1-VLP probes were tested on the ability to pack and deliver the reporter plasmid into Cos7 (green monkey kidney cells) cells in vitro, since this cell line is known to be transducible by JCV VLPs. There were 9 salt precipitated VP1-VLPs probes and 15 chromatographic purified VP1-VLPs probes. The transduction experiments in vitro were 5 times repeated. In this experiments, the ability to deliver maximum luminescence signal with the Luciferin substrates for in vivo experiments were tested.

Salt precipitated VP1-VLPs were overnight precipitated and dialysed 24 hours against the Standard Buffer (150 mM NaCl, 10 mM Tris-HCl, pH7.5). The packaging of the Reporter gene plasmid was achieved by chemical dissociation and reassociation as described in Goldmann et al., 1999, Journal of Virology: Molecular cloning and expression of major structural protein VP1 of the human polyoma virus: formation of virus like particles useful for immunological and therapeutic studies.

The Experimental Layout

Intravenous injection of VLPs into immunocompetent BALB/c mice was conducted in the tail vein under isoflurane anesthesia.

The animals were grouped as following:
5 µg salt precipitated VLPs (4 animals)
50 µg salt precipitated VLPs (4 animals)
5 µg chromatographic purified VLPs (4 animals)
DNA control (the reporter gene plasmid only) (3 animals)
VLPs control (the VP1-VLP capsids only) (3 animals)

The bioluminescence was measured on day 2, 4, 7, 14 and 22, 12 min after intraperitoneal injection of the Luciferin substrate. The results were pooled in each group and the average result and the standard deviation were calculated. The averages were analysed with Two-Way-ANOVA with Holm-Sidak-Test as posthoc-test.

Figure 3:
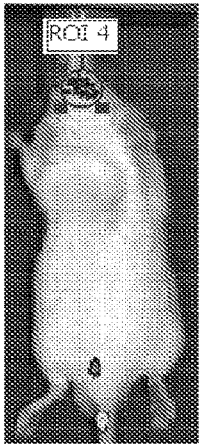
Figure 4:
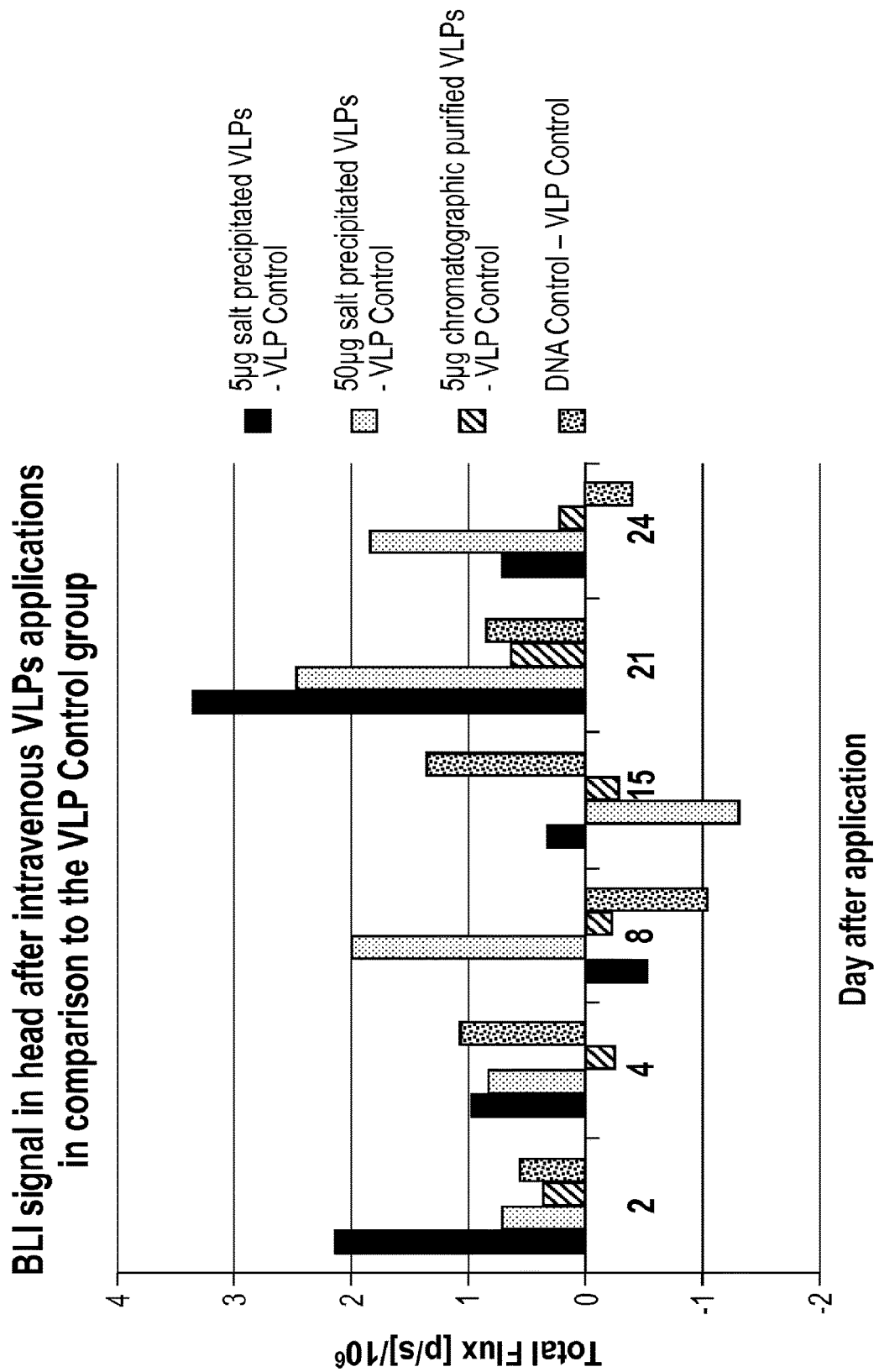

Results are shown in FIGS. 3 and 4

2. Transduction Efficacy of Cos7 Cells (African Green Monkey Kidney Cells) with Help of the Luciferase Plasmids Loaded JC VP1-VLPs and JC VP1-VLPs Mixed with Luciferase Plasmids 18 hours before the Transduction Cos7 Cells were passaged into 24-Well plate.

VP1-VLPs were dissociated with DTT and EGTA, mixed with the Luciferase plasmid and dialysed against re-association Buffer overnight by +4° C.

On the next day, packed VP1-VLPs were taken out of Dialysis.

The mixed VP1-VLPs with Luciferase plasmid were prepared according to Krauzewicz (Gene Therapy (2000) 7, 1094-1102):

VLPs to Luciferase plasmid Ratio mix were 30:1 (w/w)
This mix was incubated 15 min by RT
The mixtures were diluted with DMEM cell media and pipetted to the Cos7 Cells in 24-Well plate.

The VP1-VLPs packed with Luciferase plasmid were pipetted to the Cos7 Cells; same was conducted with VP1-VLPs mixed with Luciferase plasmid.

After 72 hours the cells were lysed and Luciferase Activity were measured in Triplets with help of Luciferase Assay from Promega.

Figure 5A:
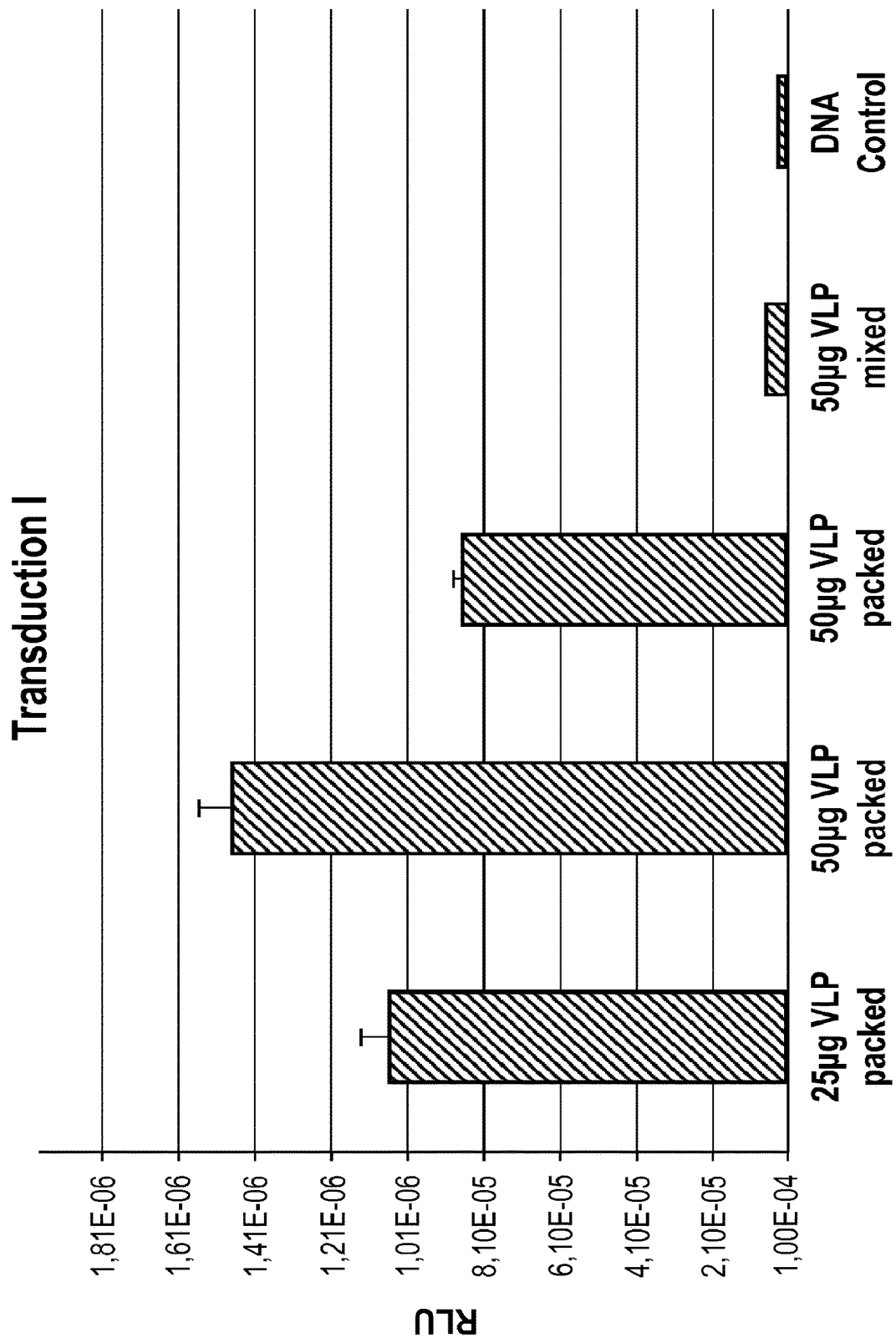
Figure 5B:
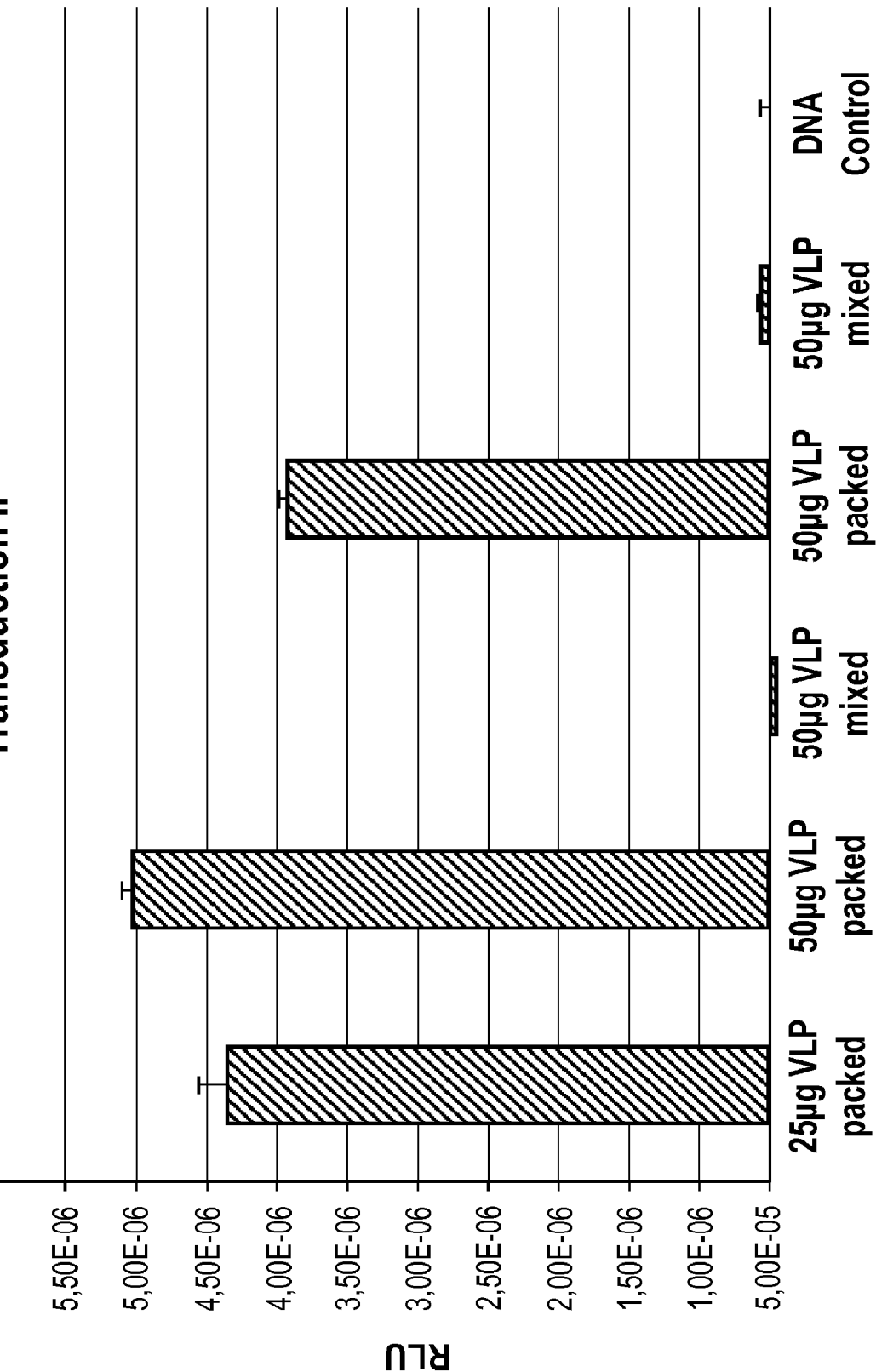

Results of to independent Transduction experiments are shown in FIG. 5

4. Immunohistochemical Detection of Luciferase and VP1 Protein in the Mouse Brain after Intravenous Application of VLPs Packed with a Luciferase Plasmid As showed above, JC VP1-VLPs are capable to deliver substances into cells and organs in the living organism as proved by detection of the plasmid DNA (by qPCR) or the Luciferase activity. These experimental results are further supported by the immunohistochemical detection of the Luciferase protein and VP1 protein in the brain.

Brain tissues were isolated from mice with an Intravenous injection of VLPs into immunocompetent BALB/c mice (treatment as described above), fixed in PFA and embedded in paraffin as described (J. Jankowski et al., The Journal of comparative Neurology 472: 87-99, 2004: "Engrailed-2 negatively regulates the onset if prenatal Purkinje Cell differentiation"). 7 to 10 µm thin sections were cut and mounted on Histobond plus slides. The sections were rehydrated, the endogen peroxidase was inactivated and the sections permeabilized. A blocking step was performed in 3% bovine serum albumin solution. Luciferase protein or VP1 protein, respectively were detected with monoclonal antibodies. To increase the signal strength the TSA amplifying fluorescent system (TSA™ Plus Fluorescein System, Perkin Elmer) was used.

Figure 6:
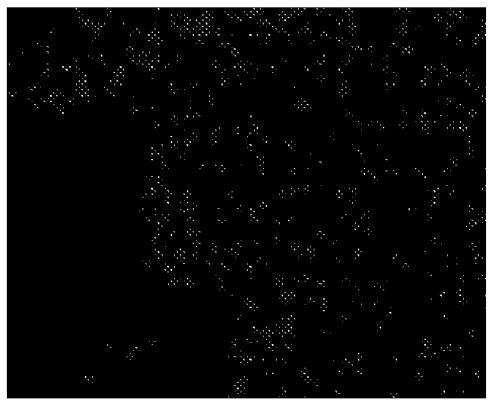
Figure 6:
Figure 6:
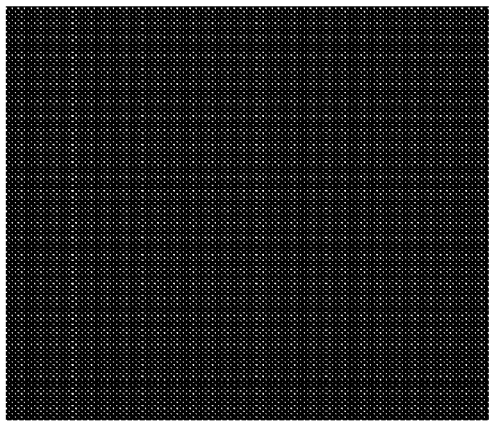
Figure 6:
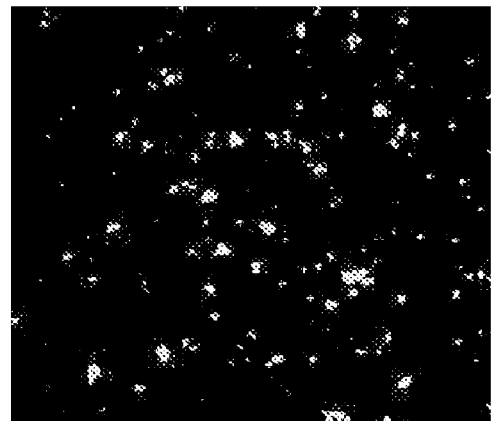
Figure 6:
Figure 6:
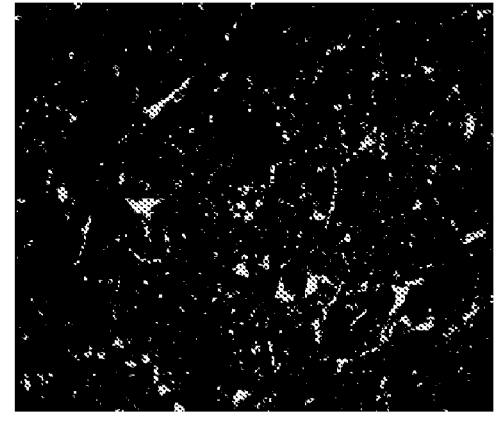
Figure 7:
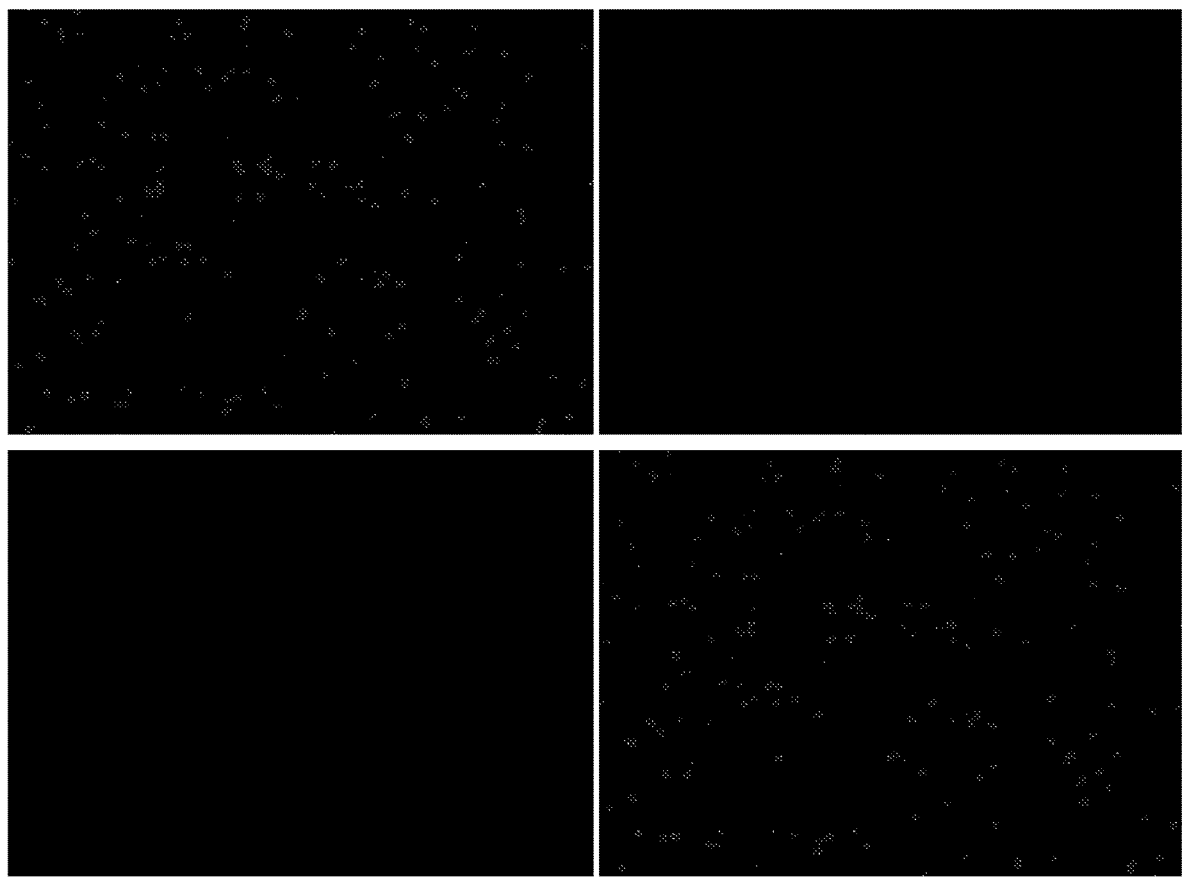

Results:

As shown in the right panel of FIG. 6 B, the immunohistochemical analysis using the anti-VP1 antibody were able to detect VP1 protein in cells of the CNS. The brain slice shows scattered spots of irregular size, which is indicative of a cellular localization of VP1 within brain parenchyma. Using the anti-Luciferase antibody, also Luciferase protein could be detected in cells of the CNS. In accordance with the results for the VP1 protein also the Luciferase-derived staining of the brain slice shows scattered spots of irregular size, which is indicative of a cellular localization of Luciferase within brain parenchyma.

Discussion:

The cellular presence of the luciferase and the VP1 protein in the brain represent a further support of the basic concept of the invention, because it demonstrates that the VLP, and not just the active substance alone, cross the BBB and enter into the CNS.

5. Colocalization Analysis Reveals Presence of VP1 Protein in Oligodendrocytes.

Based on the above described cellular detection of VP1 protein in the CNS, a co-localization experiment was performed in order to identify the respective target cells. For this purpose, the detected VP1 protein was co-localized with the marker Olig 2, which is specifically located on oligodendrocytes (B. Menn et al., "Origin of oligodendrocytes in the subventricular zone of the adult brain", The Journal of Neuroscience, 2006, 26(30): 7907-7918).

Figure 8:
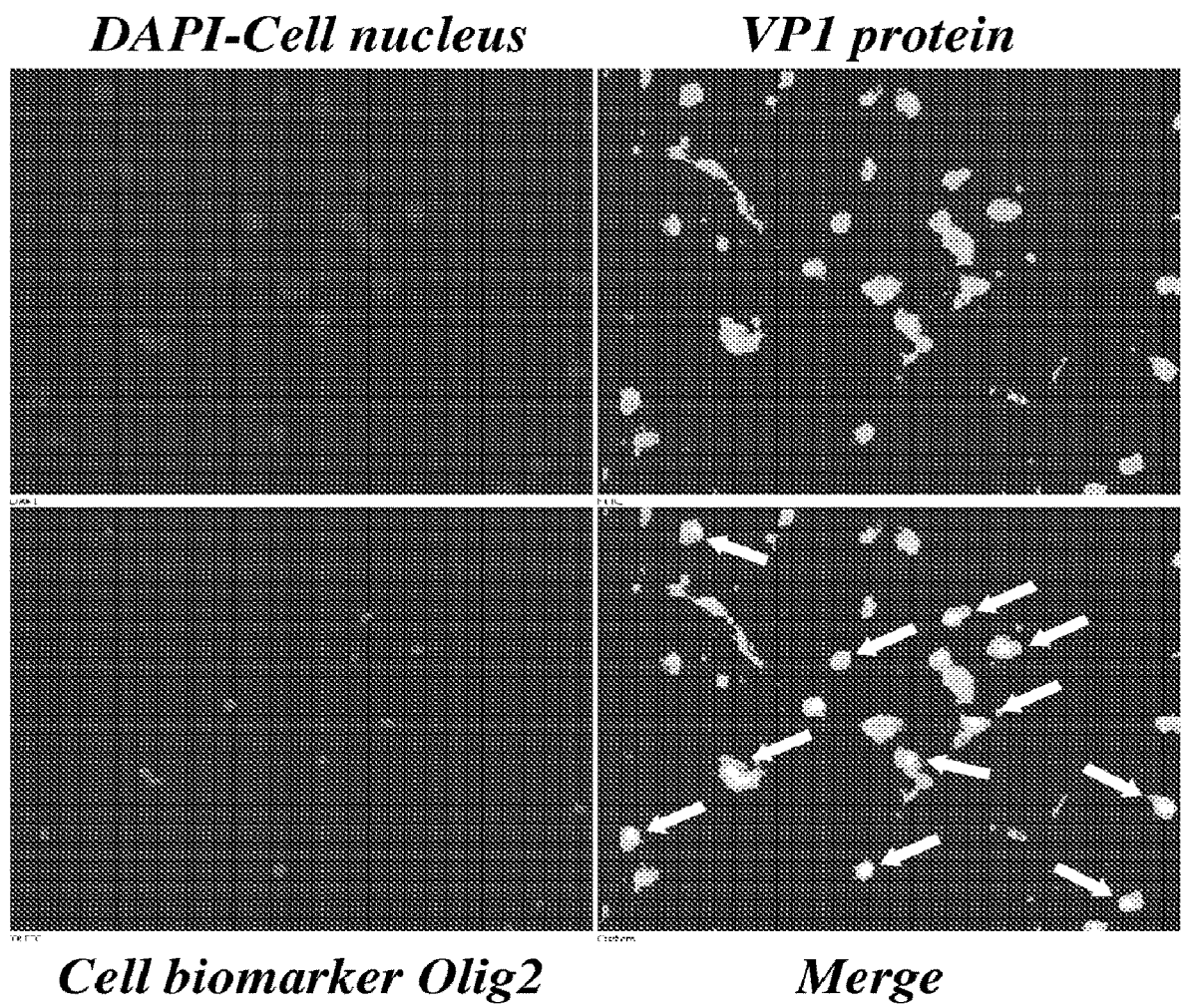

Results:

As shown in the lower left panel of FIG. 8, by using the Olig2 marker several irregular spots could be detected in the brain slice, which in every case are also stained by the nucleus stain DAPI (upper left panel of FIG. 8) and therefore indicative of oligodendrocytes. Each of these oligodendrocytes is also positive for VP1 protein as shown in the lower right panel of FIG. 8. The cells which are positive for Olig2 and VP1 are marked with a white arrow. Hence, the VP1 protein is localized in CNS oligodendrocytes, which is indicative for a infection of these cells by the intravenously applied VLPs.

Discussion:

The detection of the VP1 protein in the brain oligodendrocytes is in line with the natural tropism of the JCV virus. As a result the claimed VLPs of the invention are especially suited for a therapeutic treatment of diseases associated with oligodendrocytes such as multiple sclerosis.

LEGEND

FIG. 1: A, B—Relative transendothelial electrical resistance development (A and B) after addition of the VP1-VLPs in concentrations between $5*10^8$ and $2*10^{12}$ particles per well (n=3).

FIG. 2: Passage of the VP1-VLPs loaded DNA through the blood-brain-barrier in the in vitro model, measured with qPCR with specific primers. Added VLPs—the number of the VLPs added on the apical side in BBB model, Detected VLPs—detected number of the plasmid on the apical and basolateral sides in BBB model (n=3)

FIG. 3: Bioluminescent signals in mice body after intravenous application: 5 μg salt precipitated VLPs; 50 μg salt precipitated VLPs; 5 μg chromatographic purified VLPs; DNA control (the reporter gene plasmid only); VLPs control (the VP1-VLP capsids only). As example, 1 mouse of each group on the ventral and dorsal side.

FIG. 4: Bioluminescent signals in mice heads after intravenous application: 5 μg salt precipitated VLPs; 50 μg salt precipitated VLPs; 5 μg chromatographic purified VLPs; DNA control (the reporter gene plasmid only). The average results in the groups minus the VLP control (as a background signal).

FIG. 5: A, B: Transduction of the Cos7 cells with help of the VP1-VLPs, loaded with Luciferase plasmid DNA. RLU—Relative Light Units; 25 μg VLP packed—25 μg JC VP1-VLPs packed with Luciferase plasmid; 50 μg VLP packed—50 μg JC VP1-VLPs packed with Luciferase plasmid; 50 μg VLP mixed—50 μg JC VP1-VLPs mixed with Luciferase plasmid; DNA Control—Luciferase plasmid Control.

FIG. 6: Immunohistochemical analysis of brain sections. Left column shows DAPI staining of the cell nucleus, right column the fluorescent labeled proteins: A—negative control; B—FITC-fluorescent staining of VP1 protein; C—FITC-fluorescent staining of Luciferase protein.

FIG. 7: Negative controls for the co-localization of VP1 protein with the oligodendrocyte marker Olig2. Upper left panel shows staining of the cell nuclei with the dye DAPI. Upper right panel shows signal after fluorescence detection without the use of the anti-VP1 antibody. Lower left panel shows signal after fluorescence detection without the use of the anti-Olig2 antibody. Lower right panel represents the merged pictures of the two control stains.

FIG. 8: Co-localization of VP1 protein with the oligodendrocyte marker Olig2. Upper left panel shows staining of the cell nuclei with the dye DAPI. Upper right panel shows the localization of the VP1 protein (FITC-fluorescence). Lower left panel shows the staining with the anti-Olig2 antibody (TRITC-fluorescence). Lower right panel represents the merged pictures of the staining for the Olig2-marker and the VP1 protein.

The invention claimed is:

1. A method of treating a central nervous system (CNS) disease or a neurological, neuronal or neurodegenerative disorder, the method comprising:

intravenously administering a drug delivery system composed of virus-like particles (VLP) loaded with a drug into a subject in need thereof, wherein said subject has a physiologically intact blood-brain barrier (BBB), wherein the VLP cross the blood-brain barrier (BBB) of the subject together with the drug, wherein the VLP are composed of VP1 comprising an amino acid sequence which is at least 80% identical to the amino acid sequence according to SEQ ID NO: 1 over its entire length, and wherein in said method, said drug delivery system does not further contain, and said subject is not administered, an additive that decreases the integrity of, or increases the permeability of, the BBB.

2. The method as recited in claim 1, wherein the drug is detectable in the CNS within two days after administration.

3. The method as recited in claim 1, wherein the method does not require a loss of integrity or an increased permeability of the BBB.

4. The method as recited in claim 1, wherein the drug delivery system crosses a physiologically intact BBB.

5. The method as recited in claim 1, wherein the drug is transported into cells of the central nervous system (CNS).

6. The method as recited in claim 1, wherein the drug is transported to oligodendrocytes or into oligodendrocytes.

7. The method as recited in claim 1, wherein the drug is selected from the group consisting of a cytotoxic agent,
a detectable agent,
a protein,
a peptide and
a nucleic acid.

8. The method as recited in claim 7, wherein the nucleic acid encodes a desired protein,
is an inhibitory nucleic acid, or
is a nucleic acid having catalytic activity.

9. The method as recited in claim 8, wherein, the detectable agent is a radionuclide,
the nucleic acid which encodes the desired protein is selected from mRNA, cDNA, a plasmid or a vector,
the inhibitory nucleic acid is siRNA or miRNA, or
the nucleic acid having catalytic activity is a ribozyme.

10. The method as recited in claim 1, wherein, the VLP comprise a hull, and
at least 1% or at least 15% or at least 50% or at least 95% of a total amount of the drug is fully encapsulated in the hull of the VLP.

11. The method as recited in claim 1, wherein the subject is a human patient.

12. The method as recited in claim 1, wherein the VLP are non-aggregated.

* * * * *

SEQUENCE LISTING

```
<160> NUMBER OF SEQ ID NOS: 5

<210> SEQ ID NO 1
<211> LENGTH: 354
<212> TYPE: PRT
<213> ORGANISM: JC polyoma virus
<220> FEATURE:
<221> NAME/KEY: MISC_FEATURE
<222> LOCATION: (1)..(354)
<223> OTHER INFORMATION: capsid protein VP1
<220> FEATURE:
```

```
<221> NAME/KEY: MISC_FEATURE
<222> LOCATION: (10)..(10)
<223> OTHER INFORMATION: Xaa is Pro or Arg

<400> SEQUENCE: 1
```

Met Ala Pro Thr Lys Arg Lys Gly Glu Xaa Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
                35                  40                  45

Gly Asp Pro Asp Glu His Leu Arg Gly Phe Ser Lys Ser Ile Ser Ile
        50                  55                  60

Ser Asp Thr Phe Glu Ser Asp Ser Pro Asn Arg Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Ser Leu Met Asn Val His Ser Asn Gly Gln Ala Thr
                115                 120                 125

His Asp Asn Gly Ala Gly Lys Pro Val Gln Gly Thr Ser Phe His Phe
        130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
            195                 200                 205

Glu Asn Thr Arg Tyr Phe Gly Thr Leu Thr Gly Gly Glu Asn Val Pro
210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
            290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Lys Tyr Gly Gln Leu Gln Thr Lys
            340                 345                 350

Met Leu

```
<210> SEQ ID NO 2
<211> LENGTH: 1065
<212> TYPE: DNA
<213> ORGANISM: JC virus
```

```
<220> FEATURE:
<221> NAME/KEY: MISC_FEATURE
<222> LOCATION: (1)..(1065)
<223> OTHER INFORMATION: capsid protein VP1

<400> SEQUENCE: 2
atggctccca ccaagcgcaa gggcgagcsc aaggayccccg tgcaagtgcc caagctgctg      60
atccgtggtg gtgtcgaggt gctggaagtc aagaccggcg tggactccat taccgaggtg     120
gagtgcttcc tcaccccga gatgggtgac cctgacgagc acctgagggg cttctccaag     180
tccatctcca tctccgacac cttcgagtcc gactcccca accgtgacat gctgccctgc     240
tactccgtgg ctcgtatccc cctgcccaac ctgaacgagg acctgacttg cggcaacatc     300
ctgatgtggg aggctgtgac cctcaagacc gaggtcatcg gcgtgacttc cctgatgaac     360
gtgcactcca acggccaggc tacccacgac aacggtgctg gcaagcccgt gcagggaacc     420
tccttccact tcttctccgt gggtggcgag gctctggaac tccagggcgt ggtgttcaac     480
taccgtacca gtaccccga cggcaccatc ttccccaaga cgctactgt gcagtcccaa     540
gtgatgaaca ccgagcacaa ggcttacctg acaagaaca aggcctaccc cgtggagtgc     600
tgggtgcccg accccacccg taacgagaac acccgttact cggcaccct gaccggtgga     660
gagaacgtgc ccccgtgct gcacatcacc aacaccgcta ccaccgtgct gctggacgag     720
ttcggtgtcg gtccctgtg caagggcgac aacctgtacc tgtccgctgt ggacgtgtgc     780
ggcatgttca ccaaccgttc cggttcccag cagtggcgtg gcctgtcccg ctacttcaag     840
gtgcagctgc gcaagcgtcg tgtgaagaac ccctacccta tctccttcct gctgaccgac     900
ctgatcaacc gtcgtacccc tcgtgtggac ggccagccca tgtacggcat ggacgctcag     960
gtggaagagg tccgcgtgtt cgagggcacc gaggaattgc ccggcgaccc cgacatgatg    1020
cgttacgtgg acaagtacgg ccagctccag accaagatgc tgtaa                    1065
```

```
<210> SEQ ID NO 3
<211> LENGTH: 344
<212> TYPE: PRT
<213> ORGANISM: JC virus
<220> FEATURE:
<221> NAME/KEY: MISC_FEATURE
<222> LOCATION: (1)..(344)
<223> OTHER INFORMATION: capsid protein VP2

<400> SEQUENCE: 3

Met Gly Ala Ala Leu Ala Leu Leu Gly Asp Leu Val Ala Thr Val Ser
1               5                   10                  15

Glu Ala Ala Ala Ala Thr Gly Phe Ser Val Ala Glu Ile Ala Ala Gly
            20                  25                  30

Glu Ala Ala Ala Thr Ile Glu Val Glu Ile Ala Ser Leu Ala Thr Val
        35                  40                  45

Glu Gly Ile Thr Ser Thr Ser Glu Ala Ile Ala Ala Ile Gly Leu Thr
    50                  55                  60

Pro Glu Thr Tyr Ala Val Ile Thr Gly Ala Pro Gly Ala Val Ala Gly
65                  70                  75                  80

Phe Ala Ala Leu Val Gln Thr Val Thr Gly Gly Ser Ala Ile Ala Gln
                85                  90                  95

Leu Gly Tyr Arg Phe Phe Ala Asp Trp Asp His Lys Val Ser Thr Val
            100                 105                 110

Gly Leu Phe Gln Gln Pro Ala Met Ala Leu Gln Leu Phe Asn Pro Glu
        115                 120                 125
```

```
Asp Tyr Tyr Asp Ile Leu Phe Pro Gly Val Asn Ala Phe Val Asn Asn
    130                 135                 140

Ile His Tyr Leu Asp Pro Arg His Trp Gly Pro Ser Leu Phe Ser Thr
145                 150                 155                 160

Ile Ser Gln Ala Phe Trp Asn Leu Val Arg Asp Asp Leu Pro Ser Leu
                165                 170                 175

Thr Ser Gln Glu Ile Gln Arg Arg Thr Gln Lys Leu Phe Val Glu Thr
                180                 185                 190

Leu Ala Arg Phe Leu Glu Glu Thr Thr Trp Ala Ile Val Asn Ser Pro
            195                 200                 205

Val Asn Leu Tyr Asn Tyr Ile Ser Asp Tyr Tyr Ser Arg Leu Ser Pro
210                 215                 220

Val Arg Pro Ser Met Val Arg Gln Val Ala Gln Arg Glu Gly Thr Tyr
225                 230                 235                 240

Ile Ser Phe Gly His Ser Tyr Thr Gln Ser Ile Asp Asn Ala Asp Ser
                245                 250                 255

Ile Gln Glu Val Thr Gln Arg Leu Asp Leu Lys Asn Pro Asn Val Gln
                260                 265                 270

Ser Gly Glu Phe Ile Glu Lys Ser Phe Ala Pro Gly Gly Ala Asn Gln
            275                 280                 285

Arg Ser Ala Pro Gln Trp Met Leu Pro Leu Leu Leu Gly Leu Tyr Gly
        290                 295                 300

Thr Val Thr Pro Ala Leu Glu Ala Tyr Glu Asp Gly Pro Asn Lys Lys
305                 310                 315                 320

Lys Arg Arg Lys Glu Gly Pro Arg Ala Ser Ser Lys Thr Ser Tyr Lys
                325                 330                 335

Arg Arg Ser Arg Ser Ser Arg Ser
            340

<210> SEQ ID NO 4
<211> LENGTH: 1032
<212> TYPE: DNA
<213> ORGANISM: JC virus
<220> FEATURE:
<221> NAME/KEY: MISC_FEATURE
<222> LOCATION: (1)..(1032)
<223> OTHER INFORMATION: capsid protein VP2

<400> SEQUENCE: 4
atgggtgccg cacttgcact ttgggggac  ctagttgcta ctgtttctga ggctgctgct      60
gccacaggat tttcagtagc tgaaattgct gctggagagg ctgctgctac tatagaagtt    120
gaaattgcat cccttgctac tgtagagggg attacaagta cctctgaggc tatagctgca    180
ataggcctta ctcctgaaac atatgctgta attactggag ctccggggc  tgtagctggg    240 tttgctgcat tggttcaaac tgtaactggt ggtagtgcta ttgctcagtt gggatataga    300 tttttttgctg actgggatca taaagtttca acagttgggc tttttcagca gccagctatg    360
gctttacagt tatttaatcc agaagactac tatgatattt tatttcctgg agtgaatgcc    420
tttgttaaca atattcacta tttagatcct agacattggg gcccttcttt gttctccaca    480
atctcccagg cttttggaa  tcttgttaga gatgatttgc catctttaac atctcaggaa    540
attcaaagaa gaacccaaaa actatttgtt gaaactttag caaggttttt ggaagaaact    600
acttgggcaa tagttaattc accagttaac ttatataatt atatttcaga ctattattct    660
agattgtctc cagttaggcc ctctatggta aggcaggttg cccaagggga gggaacctat    720
atttcctttg gccactcata cacccaaagt atagataatg cagacagcat tcaagaagtt    780
```

-continued

```
acccaaaggc tagatttaaa aaacccaaat gtgcaatctg gtgaatttat agagaaaagt    840
tttgcaccag gaggtgcaaa tcaaagatct gctcctcaat ggatgttgcc tttactttta    900
gggttgtacg ggactgtaac acctgctctt gaagcatatg aagatggccc caacaaaaag    960
aaaaggagaa aggaaggacc ccgtgcaagt tccaaaactt cttataagag gaggagtaga   1020
agttctagaa gt                                                       1032

<210> SEQ ID NO 5
<211> LENGTH: 8
<212> TYPE: PRT
<213> ORGANISM: Artificial
<220> FEATURE:
<223> OTHER INFORMATION: nuclear localization signal

<400> SEQUENCE: 5

Cys Pro Gly Ala Ala Pro Lys Lys
1               5
```